(12) United States Patent
Yang et al.

(10) Patent No.: US 10,557,176 B2
(45) Date of Patent: Feb. 11, 2020

(54) METHOD FOR DETECTING TRACE FUNGI USING SINGLE-CELL SEQUENCING AND KIT THEREOF

(71) Applicant: Beijing Institute of Radiation Medicine, Beijing (CN)

(72) Inventors: Ying Yang, Beijing (CN); Shengqi Wang, Beijing (CN); Zhe Zhou, Beijing (CN); Min Chen, Beijing (CN); Peng Wang, Beijing (CN); Zhen Li, Beijing (CN); Zongwei Li, Beijing (CN)

(73) Assignee: BEIJING INSTITUTE OF RADIATION MEDICINE, Beijing (CN)

( * ) Notice: Subject to any disclaimer, the term of this patent is extended or adjusted under 35 U.S.C. 154(b) by 0 days.

(21) Appl. No.: 16/313,906

(22) PCT Filed: Aug. 5, 2016

(86) PCT No.: PCT/CN2016/093734
§ 371 (c)(1),
(2) Date: Dec. 28, 2018

(87) PCT Pub. No.: WO2018/006458
PCT Pub. Date: Jan. 11, 2018

(65) Prior Publication Data
US 2019/0323092 A1 Oct. 24, 2019

(30) Foreign Application Priority Data
Jul. 8, 2016 (CN) .......................... 2016 1 0535044

(51) Int. Cl.
*C12Q 1/6895* (2018.01)
*C12N 15/10* (2006.01)
(Continued)

(52) U.S. Cl.
CPC ........... *C12Q 1/6895* (2013.01); *C12N 15/10* (2013.01); *C12Q 1/6869* (2013.01)

(58) Field of Classification Search
CPC . C12N 15/10; C12Q 1/04; C12Q 1/68; C12Q 1/6806; C12Q 1/6869; C12Q 1/6895; C12R 1/645
See application file for complete search history.

(56) References Cited

U.S. PATENT DOCUMENTS

2010/0047768 A1  2/2010  Williamson et al.

FOREIGN PATENT DOCUMENTS

| CN | 101712932 A | 5/2010 |
| CN | 103194440 A | 7/2013 |

(Continued)

OTHER PUBLICATIONS

Haoxiang SU, Preliminary search of single cell sequencing technique in pathogen detection, Medicine & public health, China master's theses full-text database, No. 01, Jan. 2015, pp. E060-107.

(Continued)

*Primary Examiner* — Jeremy C Flinders
(74) *Attorney, Agent, or Firm* — Gokalp Bayramoglu

(57) ABSTRACT

A method for detecting trace fungi using single-cell sequencing and a fungi detection kit prepared by the method are disclosed. The method includes the steps of obtaining trace fungal cells, extracting fungal protoplasm by breaking the cell walls of fungi, extracting gDNA from trace fungal protoplasm and amplifying the gDNA, constructing trace gDNA library, genome sequencing, bioinformatics analysis and comparison, and determining the species of detected fungi, etc. The method realizes the high-efficiency detection of trace fungi, and can be directly applied to the isolation, detection, identification of trace and difficult-to-identify fungal samples or mixed samples, and in-depth study of genetic information. The fungi detection method and the kit are applicable to industrial production, environmental monitoring, air testing, soil testing, water quality testing, food (Continued)

testing, drug testing, cosmetics testing, health care products testing and medical testing, and other fields.

20 Claims, 1 Drawing Sheet

(51) Int. Cl.
*C12Q 1/6869* (2018.01)
*C12N 1/10* (2006.01)

(56) References Cited

FOREIGN PATENT DOCUMENTS

| CN | 104178431 A | 12/2014 |
| CN | 105039183 A | 11/2015 |

OTHER PUBLICATIONS

Mingken Wei et al., Preparing high quality protoplast of Candida albicans by snailase, Guangdong agricultural sciences, No. 9, Dec. 31, 2012, pp. 99-102, Abstract only.

Paul C. Blainey et al., Genome of a Low-Salinity Ammonia-Oxidizing Archaeon Determined by Single-Cell and Metagenomic Analysis, PLoS ONE, Feb. 22, 2011, vol. 6, No. 2, p. e16626.

Thomas Ishoey et al., Genomic sequencing of single microbial cells from environmental samples, Curr opin microbiol, Jun. 30, 2008, vol. 11, No. 3, pp. 198-204.

Yunwei Wang et al., Laser capture microdissection and metagenomic analysis of intact mucosa-associated microbial communities of human colon, Appl Microbiol Biotechnol, vol. 88, No. 6, Oct. 8, 2010, pp. 1333-1342.

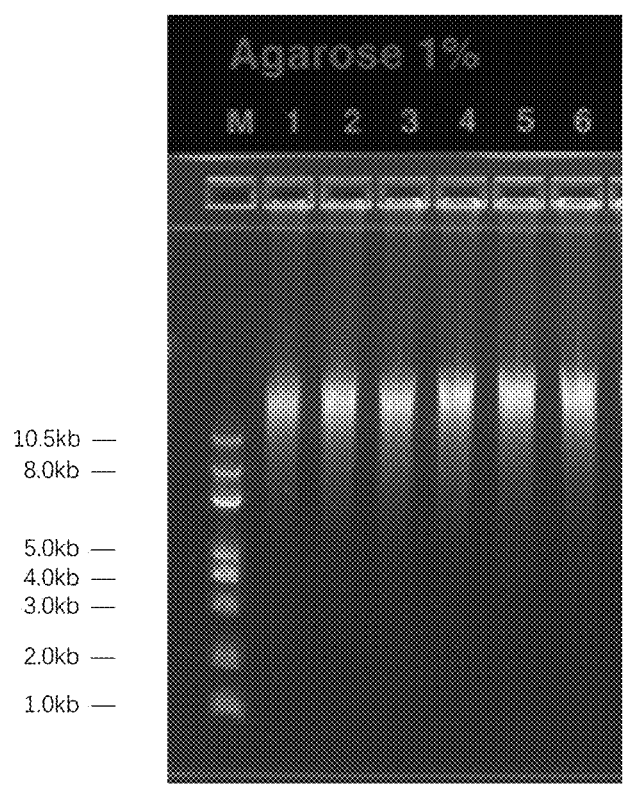

METHOD FOR DETECTING TRACE FUNGI USING SINGLE-CELL SEQUENCING AND KIT THEREOF

CROSS REFERENCE TO RELATED APPLICATIONS

This application is the national phase entry of International Application No. PCT/CN2016/093734, filed on Aug. 5, 2016, which is based upon and claims priority to Chinese Application No. 201610535044.3, filed on Jul. 8, 2016, the entire contents of which are incorporated herein by reference.

TECHNICAL FIELD

The present invention relates to the field of microbiology and molecular biology, and particularly to a method for detecting trace fungi using a single-cell sequencing and a fungi detection kit prepared by the method.

BACKGROUND

1. Overview of Existing Single-Cell Sequencing Technology

1) At present, single-cell sequencing technology is mainly used for the study of the development of human or mammalian embryonic cells and stem cells. Such cells only have cell membranes and have no cell walls, so it is not necessary to break the walls, and is relatively easy to extract gDNA from trace cells.

2) It is reported that single-cell sequencing technology is used for the study of plant seed development and cell sequencing of plant endophytic fungi. Such cells can be isolated and cultured, so it is relatively easy to obtain pure cell lines for molecular detection experiments.

2. Overview of Existing Fungal Wall-Breaking and DNA Extraction Technologies

1) Physical method: liquid nitrogen is added into a mortar for grinding, or a grinder is used for a low-temperature grinding. However, a large number of fungi are required in this method, thus the method cannot be applied to trace samples.

2) Chemical method: benzyl chloride extraction method, etc. The extracted DNA is poor in integrity and degrades easily. Generally, the DNA extracted by this method is only enough for PCR amplification, it is difficult to achieve the integrity requirements for the use in the construction of the gene libraries.

3) Enzymatic method: snail enzyme, cellulase, lysozyme, lywallzyme, etc. This method has low efficiency, and the amount of DNA extracted is not enough for trace samples to construct gene libraries.

3. Overview of Existing Detection Techniques for Trace Fungal Samples:

1) Microscopic examination: Direct observation under the microscope. Although the method is simple and fast, it has low sensitivity and some fungi may get missed easily, thus requiring rich operational experience.

2) Culture: The morphology and biochemical indicators of fungi in the culture process can be used as important standards for detection, but it is time-consuming and can get contaminated easily, and many fungi (especially pathogenic fungi) are difficult to be successfully cultured under artificial culture conditions.

3) PCR and gene chip technology: It is suitable for fungal detection with a clear range, which requires to design the primers and probes specifically, and this technology is not suitable for completely unknown species.

4) First-generation sequencing after PCR amplification using universal primers: It is suitable for the detection of single unknown fungi, generally applicable for detection of cultivable pure fungi, and is not suitable for detection of complex samples at one time.

5) Application of next-generation metagenome sequencing: It can be used for the detection of complex samples. However, since it is difficult to extract the DNA of fungi as compared to that of other microorganisms or mammals, a large amount of data irrelevant to the target species will be generated, making it very difficult to identify the data.

According to the above overviews of the prior art, it can be seen that the current detection techniques for trace fungi mainly have the following technical disadvantages.

1. It is difficult to perform efficient wall-breaking on trace fungi, non-cultivable fungi or difficult-to-culture fungi.

2. It is difficult to extract a sufficient amount of gDNA that can be used for the construction of gene libraries from trace fungi.

3. It is difficult to detect specific fungi in complex samples.

In conclusion, the extraction of complete genomic DNA by breaking the fungal wall has been a difficult problem in the field, especially for trace fungal samples. How to extract the fungal gDNA to reach the amount required for library construction for the second-generation sequencing from trace complex samples, and to perform the whole genome sequencing on the fungal gDNA have not been reported yet.

The method of the present invention can well overcome the above-mentioned technical defects by performing the steps of performing wall-breaking treatment on trace fungal cells, extracting gDNA, amplifying the gDNA, constructing the libraries for next-generation sequencing and performing genome sequencing and analysis, thereby realizing the high-efficiency detection of the trace fungi. The method of the present invention can be directly applied to the isolation, detection, identification of trace fungal samples, difficult-to-identify fungal samples or mixed samples, and in-depth study of genetic information. The fungi detection kit prepared according to the method of the present invention can be widely applied in various fields such as industrial production, environmental monitoring, air testing, soil testing, water quality testing, food testing, drug testing, cosmetics testing, health care products testing and medical testing, etc. The popularization and application of the technology of the present invention will have a good market prospect and generate considerable economic and social benefits.

SUMMARY

Technical Problems to be Solved

The problems to be solved by the present invention is as follows: the objective of the present invention is to overcome the deficiencies of the existing detection technology of trace fungi, such as difficulty in performing high-efficiency wall-breaking treatment on trace fungi, non-cultivable fungi or difficult-to-culture fungi, difficulty in extracting a sufficient amount of gDNA required for the construction of the gene libraries from trace fungi, difficulty in detecting specific fungi in complex samples, and other problems.

Technical Solutions

The present invention aims at establishing a complete set of technical solution for the detection of trace fungi, so as to solve the existing technical problems such as difficulty in isolating and culturing trace fungi from complex samples, and difficulty in performing molecular detection and genetic information research on the trace fungi in complex samples by conventional methods.

By performing the isolation and acquisition of a fungal single-cell from complex samples and extraction of the protoplasm of the fungal single-cell, especially the high-efficiency breaking on the fungal cell wall, performing the extraction, amplification and library construction of the gDNA on the above-mentioned fungal protoplasm, and combining with the next-generation sequencing technology to analyze the genomic information, instead of the traditional PCR or gene chip level detection and analysis of single or multiple specific sequences, the method of the present invention achieves the accurate detection of the fungi.

First, the present invention provides a method for detecting trace fungi using a single-cell sequencing, including the following steps.

(1) Acquisition of trace fungal cells: coating the trace fungi samples onto the membrane glass slide for laser microdissection, and finding the target cell using a laser microdissection system, and performing the laser microdissection on the selected fungal single-cell with a laser power of 37-43 micro joules to obtain a single target cell. The above operation is repeated to obtain a total of 1-100 target cells.

(2) Wall-breaking of fungal cell walls: extraction of fungal protoplasm by chemical method combined with mixed enzymatic method:

1) adding 0.8 M D-sorbitol solution into a centrifuge tube containing the above-mentioned target cells to immerse the target cells at 4° C. for 2 h;

2) preparation of a composite pretreatment agent: mixing 50 mM Tris (Tris (hydroxymethyl) aminomethane), 5 mM EDTA (Ethylenediaminetetraacetic acid) and 5% β-mercaptoethanol evenly;

3) preparation of a mixed enzyme treatment agent: mixing at least two of the four enzymes including snail enzyme (1-10 mg/mL), lywallzyme (1-10 mg/mL), lysozyme (1-10 mg/mL), and cellulase (1-10 mg/mL) in a specific ratio, when the mixed enzyme treatment agent is composed of only two enzymes, at least one of the snail enzyme and the lywallzyme is included in the mixed enzyme treatment agent;

4) adding the above-mentioned composite pretreatment agent into the centrifuge tube containing the target cells to treat the target cells at 35° C. for 1 h;

5) subjecting the above-mentioned centrifuge tube to a centrifugation to collect the cells at the bottom of the centrifuge tube, then discarding the composite pretreatment agent;

6) adding sterile water into the above-mentioned centrifuge tube to wash the cells twice, centrifuging, and discarding the liquid;

7) adding the mixed enzyme treatment agent into the above-mentioned centrifuge tube to treat the cells at 35-45° C. for 3-12 h;

8) subjecting the above-mentioned centrifuge tube to a centrifugation to collect the cells at the bottom of the centrifuge tube, then discarding the liquid; and 9) adding PBS (phosphate-buffered saline) into the above-mentioned centrifuge tube to wash the cells once, centrifuging, discarding the liquid, and retaining 4-10 μl of cell suspension.

(3) Extraction gDNA from the trace fungal protoplasm and amplification of the gDNA: using a single-cell whole genome amplification kit to perform the nucleic acid extraction and amplification reaction on the 4-10 μl cell suspension obtained in the above step to obtain the above-mentioned fungal gDNA.

(4) Library construction of trace gDNA: constructing a library of the above-mentioned fungal gDNA using a DNA library construction kit.

(5) Genome sequencing: performing whole genome sequencing on the fungal gDNA after constructing the library.

(6) Bioinformatics analysis: assembling the data obtained from sequencing by using relevant software to obtain assembly results, and comparing the assembly results with the relevant public database to determine the species of the detected fungi.

Further, the fungi capable of being detected by the method of the present invention include *Candida albicans, Candida glabrata, Candida krusei, Candida tropicalis, Candida parapsilosis*, and *Candida dubliniensis*, within the genus *Candida; Aspergillus fumigatus, Aspergillus flavus, Aspergillus terreus, Aspergillus nidulans, Aspergillus niger*, and *Aspergillus ustus*, within the genus *Aspergillus; Cryptococcus neoformans* and *Cryptococcus gattii*, within the genus *Cryptococcus*; and variants of the above-mentioned species. The above-mentioned various species and their variants belong to the pathogenic bacteria in clinical medicine. Although they can be cultured in vitro, they are difficult to be isolated and cultured successfully from real clinical samples due to the drug-use in patients and other factors.

Further, the fungi capable of being detected by the method of the present invention further include *Malassezia* sp., this species is a difficult-to-culture fungus that requires strict culture conditions. Special nutrients need to be supplemented to the medium so that the *Malassezia* sp. can be cultured successfully.

Further, the fungi capable of being detected by the method of the present invention further include *Histoplasma* sp., *Emmonsia* sp., *Sporothrix schenckii, Penicillium marneffei, Paracoccidioides brasiliensis, Blastomycosis dermatitidis*, and *Coccidioides immitis*. The above-mentioned species are difficult to be successfully cultured in vitro.

As a preferred solution, in the wall-breaking of fungal cell walls in the step (2) of the method of the present invention: extraction of fungal protoplasm by chemical method combined with mixed enzymatic method, the prepared mixed enzyme treatment agent is composed of 6 mg/mL snail enzyme and 4 mg/mL lywallzyme; the mixed enzyme treatment agent is added to the centrifuge tube to treat the cells at 37° C. for 6 h; and 4 μl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 6 mg/mL snail enzyme and 4 mg/mL lysozyme; the mixed enzyme treatment agent is added to the centrifuge tube to treat the cells at 45° C. for 10 h; and finally, 5 μl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 4 mg/mL snail enzyme, 4 mg/mL lywallzyme and 4 mg/mL lysozyme; the mixed enzyme treatment agent is added to the centrifuge tube to treat the cells at 35° C. for 8 h; and finally, 6 µl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 4 mg/mL snail enzyme, 3 mg/mL lywallzyme and 3 mg/mL cellulase; the mixed enzyme treatment agent is added to the centrifuge tube to treat the cells at 37° C. for 3 h; and finally, 6 µl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 4 mg/mL snail enzyme, 3 mg/mL lysozyme and 3 mg/mL cellulase; the mixed enzyme treatment agent is added to the centrifuge tube to treat the cells at 37° C. for 12 h; and finally, 8 µl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 5 mg/mL lywallzyme, 4 mg/mL lysozyme and 3 mg/mL cellulase; the mixed enzyme treatment agent is added to the centrifuge tube to treat the cells at 37° C. for 6 h; and finally, 10 µl of cell suspension is eventually retained.

As another preferred solution, in the wall-breaking of fungal cell walls in the step (2) of the method of the present invention: extraction of fungal protoplasm by chemical method combined with mixed enzymatic method, the prepared mixed enzyme treatment agent is composed of 4 mg/mL snail enzyme, 2 mg/mL lywallzyme, 3 mg/mL lysozyme and 4 mg/mL cellulase; the mixed enzyme treatment agent is added to the centrifuge tube to treat the cells at 37° C. for 6 h; and finally, 6 µl of cell suspension is eventually retained.

In addition, the present invention further provides a fungi detection kit prepared according to the trace fungi detection method of the present invention. The fungi detection kit can be applied to the following fields: industrial production, environmental monitoring, air testing, soil testing, water quality testing, food testing, drug testing, cosmetics testing, health care products testing, and medical testing.

Beneficial Effects

The trace fungi detection method and the corresponding kit of the present invention overcome many shortcomings of the prior art, provide a solution for isolating and obtaining difficult-to-culture fungi from complex samples, provide an optimized technical solution for the efficient wall-breaking of trace fungi, and provide a complete set of technical solution for the genome sequencing analysis of trace fungi in complex samples, finally realizing high-efficiency detection of trace fungi. The method of the present invention can be directly applied to the isolation, detection, identification of trace fungal samples, difficult-to-identify fungal samples or mixed samples, and in-depth study of genetic information. The fungi detection kit prepared according to the method of the present invention can be widely applied in various fields such as industrial production, environmental monitoring, air testing, soil testing, water quality testing, food testing, drug testing, cosmetics testing, health care products testing and medical testing, etc. The popularization and application of the technology of the present invention will have a good market prospect and generate considerable economic and social benefits.

BRIEF DESCRIPTION OF THE DRAWINGS

FIG. 1 is an electrophoresis diagram of quality control detection of DNA, in which: "M" is a DNA marker, Nos. 1-3 are positive controls of gDNA that can construct libraries, and Nos. 4-6 are gDNA samples extracted from fungal single-cell in the experiment; samples and positive controls both have an obvious DNA band of larger than or equal to 10 kb.

DETAILED DESCRIPTION OF THE EMBODIMENTS

The implementation modes of the present invention will be described below with reference to specific embodiments, and those skilled in the art can readily understand other advantages and effects of the present invention from the disclosure of the present specification. The present invention can also be implemented or applied through various specific implementation modes. The various details of the present invention can be variously modified or changed without departing from the spirit of the present invention, based on various views and applications.

Before further describing the implementation modes of the present invention, it shall be understood that the scope of the present invention is not limited to the following specific embodiments. It shall also be understood that the terms used in the embodiments of the present invention are intended to describe specific implementation modes rather than limit the protective scope of the present invention. In the specification and claims of the present invention, unless otherwise explicitly stated therein, singular forms "a/an", "one" and "the/this" include plural forms.

When numerical ranges are provided by an embodiment, it shall be understood that, unless otherwise specified by the present invention, two endpoints of each numerical range and any value between the two endpoints are optional. Unless otherwise defined, all technical and scientific terms used in the present invention have the same meaning as commonly understood by those skilled in the art. In addition to the specific methods, devices, and materials used in the embodiments, according to the mastery of the prior art by those skilled in the art and the description of the present invention, any methods, devices, and materials in the prior art that are similar or equivalent to the methods, devices, and materials described in the embodiments of the present invention can also be used to realize the present invention.

Embodiment 1

1. Acquisition of cells of trace *Cryptococcus gattii*: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 40 micro joules (the range of laser power is 40±3) and is placed into a sterile centrifuge tube. The above-mentioned operations are repeated to obtain a total of 10 fungal cells (the number of cells available ranges from 1 to 100).

2. Wall-breaking of cells of *Cryptococcus gattii*: extraction of fungal protoplasm is performed by chemical method combined with mixed enzymatic method:

1) 200 μl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 6 mg/mL snail enzyme, and 4 mg/mL lywallzyme are mixed;

4) 200 μl of the composite pretreatment agent is added into the centrifuge tube to treat the cells at 35° C. for 1 h;

5) the cells are collected to the bottom of the centrifuge tube by centrifugation at 5000 rpm for 5 min, then the treatment agent is discarded;

6) 200 μl of sterile water is added to wash the cells twice, centrifugation is performed at 5000 rpm for 5 min, and the liquid is discarded;

7) 200 μl of the mixed enzyme treatment agent is added to treat the cells at 37° C. for 6 h;

8) the cells are collected to the bottom of the centrifuge tube by centrifugation at 5000 rpm for 5 min, then the liquid is discarded; and 9) 50 μl PBS is added to wash the cells once, centrifugation is performed at 5000 rpm for 5 min, the liquid is discarded, and 4 μl of cell suspension is retained.

3. Extraction gDNA from the protoplasm of the trace *Cryptococcus gattii* and amplification of the gDNA:

continued above, the 4 μl of cell suspension in the step 2, is added with 3 μl Buffer D2 of the REPLI-g Single Cell Kit (Qiagen, Germany), then mixed evenly and centrifuged instantly, incubation is performed at 65° C. for 10 min; subsequently, 3 μl Stop Solution of the Kit is added, then mixed evenly and centrifuged instantly, and temporarily stored on ice; for each amplification reaction, 40 μl PCR reaction solution (PCR reaction solution is prepared according to the manual of the kit: $H_2O$ sc 9 μl, REPLI-g sc Reaction Buffer 29 μl, REPLI-g sc DNA Polymerase 2 μl; and the sc is the abbreviation for single cell) is added to perform the reaction at 30° C. for 8 h; REPLI-g DNA polymerase is inactivated at 65° C. for 3 min, then the extracted gDNA of *Cryptococcus gattii* is obtained.

After performing the extraction of gDNA from the 10 cells of *Cryptococcus gattii* and the amplification of the gDNA, the gDNA reaches the library construction requirements of second-generation sequencing according to a DNA quality control detection. The OD260/OD280 ratio is 1.82, DNA concentration is 75 ng/μl, DNA integrity is larger than 10 kb. As shown in FIG. 1, in which: “M” is a DNA marker, Nos. 1-3 are positive controls of gDNA that can construct libraries, and Nos. 4-6 are gDNA samples extracted from fungal single-cell in the experiment; samples and positive controls both have an obvious DNA band of larger than or equal to 10 kb. The above results indicate that the DNA extraction and amplification experiment of single cells is successful; and the DNA can meet the library construction requirements of the second-generation sequencing, and can be subjected to a whole genome sequencing.

4. Library construction of trace gDNA:

a library construction is performed on the gDNA of *Cryptococcus gattii* according to the kit manual of the NEBNext® UltraDNA Library Prep Kit for Illumina® (NEB, USA).

5. Next-generation genome sequencing:

the whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

the sequencing data is assembled by using SPAdes software, and the assembled results are compared with NCBI-NT public database; and the species is determined as *Cryptococcus gattii.*

Embodiment 2

1. Acquisition of cells of trace *Candida dubliniensis*: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 43 micro joules (the range of laser power is 40±3) and is placed into a sterile centrifuge tube to obtain a total of 1 fungal cell (the number of cells available ranges from 1 to 100).

2. Wall-breaking of cell of *Candida dubliniensis*: extraction of fungal protoplasm is performed by chemical method combined with mixed enzymatic method:

1) 200 μl of 0.8 M D-sorbitol solution is added into the above-mentioned centrifuge tube to immerse the cell at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 6 mg/mL snail enzyme, and 4 mg/mL lysozyme are mixed;

4) 200 μl of the composite pretreatment agent is added into the centrifuge tube to treat the cell at 35° C. for 1 h;

5) the cell is collected to the bottom of the centrifuge tube by centrifugation at 5000 rpm for 5 min, then the treatment agent is discarded;

6) 200 μl of sterile water is added to wash the cell twice, centrifugation is performed at 5000 rpm for 5 min, and the liquid is discarded;

7) 200 μl of the mixed enzyme treatment agent is added to treat the cell at 45° C. for 10 h;

8) the cell is collected to the bottom of the centrifuge tube by centrifugation at 5000 rpm for 5 min, then the liquid is discarded; and 9) 50 μl PBS is added to wash the cell once, centrifugation is performed at 5000 rpm for 5 min, the liquid is discarded, and 5 μl of cell suspension is retained.

3. Extraction gDNA from the protoplasm of the trace *Candida dubliniensis* and amplification of the gDNA:

continued above, the 5 μl of cell suspension in the step 2 is added with 3 μl Buffer D2 of the REPLI-g Single Cell Kit (Qiagen, Germany), mixed evenly and centrifuged instantly, incubation is performed at 65° C. for 10 min; subsequently, 3 μl Stop Solution of the Kit is added, mixed evenly and centrifuged instantly, and temporarily stored on ice; for each amplification reaction, 40 μl PCR reaction solution (PCR reaction solution is prepared according to the manual of the kit: $H_2O$ sc 9 μl, REPLI-g sc Reaction Buffer 29 μl, REPLI-g sc DNA Polymerase 2 μl; and the sc is the abbreviation for single cell) is added to perform the reaction at 30° C. for 8 h; REPLI-g DNA polymerase is inactivated at 65° C. for 3 min, then the extracted gDNA of *Candida dubliniensis* is obtained.

4. Library construction of trace gDNA:

A library construction is performed on the gDNA of *Candida dubliniensis* according to the kit manual of the NEBNext® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Candida dubliniensis*.

Embodiment 3

1. Acquisition of cells of trace *Malassezia* sp.: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 38 micro joules (the range of laser power is 40±3) and is placed into a sterile centrifuge tube, the above-mentioned operations are repeated to obtain a total of 60 fungal cells (the number of cells available ranges from 1 to 100).

2. Wall-breaking of cells of *Malassezia* sp.: extraction of fungal protoplasm is performed by chemical method combined with mixed enzymatic method:

1) 200 µl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 4 mg/mL snail enzyme, 4 mg/mL lywallzyme, and 4 mg/mL lysozyme are mixed;

4) 200 µl of the composite pretreatment agent is added into the centrifuge tube to treat the cells at 35° C. for 1 h;

5) the cells are collected to the bottom of the centrifuge tube by centrifugation at 5000 rpm for 5 min, then the treatment agent is discarded;

6) 200 µl of sterile water is added to wash the cells twice, centrifugation is performed at 5000 rpm for 5 min, and the liquid is discarded;

7) 200 µl of the mixed enzyme treatment agent is added to treat the cells at 35° C. for 8 h;

8) the cells are collected to the bottom of the centrifuge tube by centrifugation at 5000 rpm for 5 min, then the liquid is discarded; and 9) 50 µl PBS is added to wash the cells once, centrifugation is performed at 5000 rpm for 5 min, the liquid is discarded, and 6 µl of cell suspension is retained.

3. Extraction gDNA from the protoplasm of the trace *Malassezia* sp. and amplification of the gDNA:

continued above, in the 6 µl of cell suspension in the step 2 is added with 3 µl Buffer D2 of the REPLI-g Single Cell Kit (Qiagen, Germany), mixed evenly and centrifuged instantly, incubation is performed at 65° C. for 10 min; subsequently, 3 µl Stop Solution of the Kit is added, mixed evenly and centrifuged instantly, and temporarily stored on ice; for each amplification reaction, 40 µl PCR reaction solution (PCR reaction solution is prepared according to the manual of the kit: $H_2O$ sc 9 µl, REPLI-g sc Reaction Buffer 29 µl, REPLI-g sc DNA Polymerase 2 µl; and the sc is the abbreviation for single cell) is added to perform the reaction at 30° C. for 8 h; REPLI-g DNA polymerase is inactivated at 65° C. for 3 min, then the extracted gDNA of *Malassezia* sp. is obtained.

4. Library construction of trace gDNA:

A library construction is performed on the gDNA of *Malassezia* sp. according to the kit manual of the NEBNext® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Malassezia* sp.

Embodiment 4

1. Acquisition of cells of trace *Emmonsia* sp.: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 40 micro joules (the range of laser power is 40±3) and is placed into a sterile centrifuge tube, the above-mentioned operations are repeated to obtain a total of 20 fungal cells (the number of cells available ranges from 1 to 100).

2. Wall-breaking of cells of *Emmonsia* sp.: extraction of fungal protoplasm is performed by chemical method combined with mixed enzymatic method:

1) 200 µl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% 3-mercaptoethanol are mixed evenly;

3) preparation of mixed enzyme treatment agent (1 ml): 4 mg/mL snail enzyme, 3 mg/mL lywallzyme, and 3 mg/mL cellulase are mixed;

4) 200 µl of the composite pretreatment agent is added into the centrifuge tube to treat the cells at 35° C. for 1 h;

5) the cells are collected to the bottom of the centrifuge tube by centrifugation at 5000 rpm for 5 min, then the treatment agent is discarded;

6) 200 µl of sterile water is added to wash the cells twice, centrifugation is performed at 5000 rpm for 5 min, and the liquid is discarded;

7) 200 µl of the mixed enzyme treatment agent is added to treat the cells at 37° C. for 3 h;

8) the cells are collected to the bottom of the centrifuge tube by centrifugation at 5000 rpm for 5 min, then the liquid is discarded; and 9) 50 µl PBS is added to wash the cells once, centrifugation is performed at 5000 rpm for 5 min, the liquid is discarded, and 6 µl of cell suspension is retained.

3. Extraction gDNA from the protoplasm of the trace *Emmonsia* sp. and amplification of the gDNA:

continued above, in the 6 µl of cell suspension in the step 2 is added with 3 µl Buffer D2 of the REPLI-g Single Cell Kit (Qiagen, Germany), mixed evenly and centrifuged instantly, incubation is performed at 65° C. for 10 min; subsequently, 3 µl Stop Solution of the Kit is added, mixed evenly and centrifuged instantly, and temporarily stored on ice; for each amplification reaction, 40 µl PCR reaction solution (PCR reaction solution is prepared according to the manual of the kit: $H_2O$ sc 9 µl, REPLI-g sc Reaction Buffer 29 µl, REPLI-g sc DNA Polymerase 2 µl; and the sc is the abbreviation for single cell) is added to perform the reaction at 30° C. for 8 h; REPLI-g DNA polymerase is inactivated at 65° C. for 3 min, then the extracted gDNA of *Emmonsia* sp. is obtained.

4. Library construction of trace gDNA:

a library construction is performed on the gDNA of *Emmonsia* sp. according to the kit manual of the NEBNext® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Emmonsia* sp.

Embodiment 5

1. Acquisition of cells of trace *Aspergillus niger*: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 37 micro joules (the range of laser power is 40±3) and is placed into a sterile centrifuge tube, the above-mentioned operations are repeated to obtain a total of 100 fungal cells (the number of cells available ranges from 1 to 100).

2. Wall-breaking of cell walls of *Aspergillus niger*: extraction of fungal protoplasm is performed by chemical method combined with mixed enzymatic method.

1) 200 μl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 4 mg/mL snail enzyme, 3 mg/mL lysozyme, and 3 mg/mL cellulase are mixed;

4) 200 μl of the composite pretreatment agent is added into the centrifuge tube to treat the cells at 35° C. for 1 h;

5) the cells are collected to the bottom of the centrifuge tube by centrifugation at 5000 rpm for 5 min, then the treatment agent is discarded;

6) 200 μl of sterile water is added to wash the cells twice, centrifugation is performed at 5000 rpm for 5 min, and the liquid is discarded;

7) 200 μl of the mixed enzyme treatment agent is added to treat the cells at 37° C. for 12 h;

8) the cells are collected to the bottom of the centrifuge tube by centrifugation at 5000 rpm for 5 min, then the liquid is discarded; and 9) 50 μl PBS is added to wash the cells once, centrifugation is performed at 5000 rpm for 5 min, the liquid is discarded, and 8 μl of cell suspension is retained.

3. Extraction gDNA from the protoplasm of the trace *Aspergillus niger* and amplification of the gDNA:

continued above, in the 8 μl of cell suspension in the step 2 is added with 3 μl Buffer D2 of the REPLI-g Single Cell Kit (Qiagen, Germany), mixed evenly and centrifuged instantly, incubation is performed at 65° C. for 10 min; subsequently, 3 μl Stop Solution of the Kit is added, mixed evenly and centrifuged instantly, and temporarily stored on ice; for each amplification reaction, 40 μl PCR reaction solution (PCR reaction solution is prepared according to the manual of the kit: $H_2O$ sc 9 μl, REPLI-g sc Reaction Buffer 29 μl, REPLI-g sc DNA Polymerase 2 μl; and the sc is the abbreviation for single cell) is added to perform the reaction at 30° C. for 8 h; REPLI-g DNA polymerase is inactivated at 65° C. for 3 min, then the extracted gDNA of *Aspergillus niger* is obtained.

4. Library construction of trace gDNA:

a library construction is performed on the gDNA of *Aspergillus niger* according to the kit manual of the NEB-Next® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Aspergillus niger*.

Embodiment 6

1. Acquisition of cells of trace *Blastomycosis dermatitidis*: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 42 micro joules (the range of laser power is 40±3) and is placed into a sterile centrifuge tube, the above-mentioned operations are repeated to obtain a total of 30 fungal cells (the number of cells available ranges from 1 to 100).

2. Wall-breaking of cell walls of *Blastomycosis dermatitidis*: extraction of fungal protoplasm is performed by chemical method combined with mixed enzymatic method:

1) 200 μl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 5 mg/mL lywallzyme, 4 mg/mL lysozyme, and 3 mg/mL cellulase are mixed;

4) 200 μl of the composite pretreatment agent is added into the centrifuge tube to treat the cells at 35° C. for 1 h;

5) the cells are collected to the bottom of the centrifuge tube by centrifugation at 5000 rpm for 5 min, then the treatment agent is discarded;

6) 200 μl of sterile water is added to wash the cells twice, centrifugation is performed at 5000 rpm for 5 min, and the liquid is discarded;

7) 200 μl of the mixed enzyme treatment agent is added to treat the cells at 37° C. for 6 h;

8) the cells are collected to the bottom of the centrifuge tube by centrifugation at 5000 rpm for 5 min, then the liquid is discarded; and 9) 50 μl PBS is added to wash the cells once, centrifugation is performed at 5000 rpm for 5 min, the liquid is discarded, and 10 μl of cell suspension is retained.

3. Extraction gDNA from the protoplasm of the trace *Blastomycosis dermatitidis* and amplification of the gDNA:

continued above, in the 10 μl of cell suspension in the step 2 is added with 3 μl Buffer D2 of the REPLI-g Single Cell Kit (Qiagen, Germany), mixed evenly and centrifuged instantly, incubation is performed at 65° C. for 10 min; subsequently, 3 μl Stop Solution of the Kit is added, mixed evenly and centrifuged instantly, and temporarily stored on ice; for each amplification reaction, 40 μl PCR reaction solution (PCR reaction solution is prepared according to the manual of the kit: $H_2O$ sc 9 μl, REPLI-g sc Reaction Buffer 29 μl, REPLI-g sc DNA Polymerase 2 μl; and the sc is the abbreviation for single cell) is added to perform the reaction at 30° C. for 8 h; REPLI-g DNA polymerase is inactivated at 65° C. for 3 min, then the extracted gDNA of *Blastomycosis dermatitidis* is obtained.

4. Library construction of trace gDNA:

A library construction is performed on the gDNA of *Blastomycosis dermatitidis* according to the kit manual of the NEBNext® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Blastomycosis dermatitidis.*

Embodiment 7

1. Acquisition of cells of trace *Coccidioides immitis*: microscopic smear and laser cutting are performed to obtain single target cell:

The trace samples are coated onto a membrane glass slide for laser microdissection (Leica Membrane Slides PEN 2.0 microns or similar product), and the target cell is found using a laser microdissection system (Leica LMD7000 or similar product) at 63 times magnification, and the selected fungal single-cell is subjected to laser microdissection by laser with a laser power of 40 micro joules (the range of laser power is 40±3) and is placed into a sterile centrifuge tube, the above-mentioned operations are repeated to obtain a total of 5 fungal cells (the number of cells available ranges from 1 to 100).

2. Wall-breaking of cell walls of *Coccidioides immitis*: extraction of fungal protoplasm is performed by chemical method combined with mixed enzymatic method.

1) 200 μl of 0.8 M D-sorbitol solution is added into the above-mentioned centrifuge tube to immerse the cells at 4° C. for 2 h;

2) preparation of composite pretreatment agent (100 ml): 50 mM Tris, 5 mM EDTA and 5% β-mercaptoethanol are mixed evenly;

3) preparation of mixed enzyme treatment agent (1 ml): 4 mg/mL snail enzyme, 2 mg/mL lywallzyme, 3 mg/mL lysozyme, and 4 mg/mL cellulase are mixed;

4) 200 μl of the composite pretreatment agent is added into the centrifuge tube to treat the cells at 35° C. for 1 h;

5) the cells is collected to the bottom of the centrifuge tube by centrifugation at 5000 rpm for 5 min, then the treatment agent is discarded;

6) 200 μl of sterile water is added to wash the cells twice, centrifugation is performed at 5000 rpm for 5 min, and the liquid is discarded;

7) 200 μl of the mixed enzyme treatment agent is added to treat the cells at 37° C. for 6 h;

8) the cells are collected to the bottom of the centrifuge tube by centrifugation at 5000 rpm for 5 min, then the liquid is discarded; and 9) 50 μl PBS is added to wash the cells once, centrifugation is performed at 5000 rpm for 5 min, the liquid is discarded, and 6 μl of cell suspension is retained.

3. Extraction gDNA from the protoplasm of the trace *Coccidioides immitis* and amplification of the gDNA:

continued above, in the 6 μl of cell suspension in the step 2 is added with 3 μl Buffer D2 of the REPLI-g Single Cell Kit (Qiagen, Germany), mixed evenly and centrifuged instantly, incubation is performed at 65° C. for 10 min; subsequently, 3 μl Stop Solution of the Kit is added, mixed evenly and centrifuged instantly, temporarily stored on ice; for each amplification reaction, 40 μl PCR reaction solution (PCR reaction solution is prepared according to the manual of the kit: $H_2O$ sc 9 μl, REPLI-g sc Reaction Buffer 29 μl, REPLI-g sc DNA Polymerase 2 μl; and the sc is the abbreviation for single cell) is added to perform the reaction at 30° C. for 8 h; REPLI-g DNA polymerase is inactivated at 65° C. for 3 min, then the extracted gDNA of *Coccidioides immitis* is obtained.

4. Library construction of trace gDNA:

A library construction is performed on the gDNA of *Coccidioides immitis* according to the kit manual of the NEBNext® UltraDNA Library Prep Kit for Illumina® (NEB, USA).

5. Next-generation genome sequencing:

The whole genome sequencing is performed on the above-mentioned gDNA which has constructed a library by using Illumina MiSeq instrument and corresponding reagents (MiSeq 600 cycles Reagent V3, Illumina, USA).

6. Bioinformatics analysis:

The sequencing data is assembled by using SPAdes software, and the assembled results are compared with NCBI-NT public database; and the species is determined as *Coccidioides immitis.*

What is claimed is:

1. A method for detecting trace fungi using a single-cell sequencing, comprising the following steps:

(1) acquisition of trace fungal cells: coating trace fungi samples onto a membrane glass slide for laser microdissection, finding target cells using a laser microdissection system, and performing the laser microdissection on one of the target cells by a laser with a laser power of 37-43 micro joules to obtain a single target cell; wherein the above operation is repeated to obtain the target cells with a total number of 1-100;

(2) wall-breaking of fungal cell walls: extraction of fungal protoplasm by a chemical method combined with a mixed enzymatic method;

1) adding 0.8 M D-sorbitol solution into a centrifuge tube containing the target cells to immerse the target cells at 4° C. for 2 h;
2) preparation of a composite pretreatment agent: mixing 50 mM Tris, 5 mM EDTA and 5% β-mercaptoethanol evenly;
3) preparation of a mixed enzyme treatment agent: preparing the mixed enzyme treatment agent according to any one of the following formula:
A: 6 mg/mL of snail enzyme and 4 mg/mL of lywallzyme,
B: 6 mg/mL of snail enzyme and 4 mg/mL of lysozyme,
C: 4 mg/mL of snail enzyme, 4 mg/mL of lywallzyme and 4 mg/mL of lysozyme,
D: 4 mg/mL of snail enzyme, 3 mg/mL of lywallzyme and 3 mg/mL of cellulase,
E: 4 mg/mL of snail enzyme, 3 mg/mL of lysozyme and 3 mg/mL of cellulase,
F: 5 mg/mL of lywallzyme, 4 mg/mL of lysozyme and 3 mg/mL of cellulase, and
G: 4 mg/mL of snail enzyme, 2 mg/mL of lywallzyme, 3 mg/mL of lysozyme and 4mg/mL of cellulase;
4) adding the composite pretreatment agent into the centrifuge tube containing the target cells to treat the target cells at 35° C. for 1 h;
5) subjecting the centrifuge tube to a centrifugation to collect the target cells to a bottom of the centrifuge tube, then discarding the composite pretreatment agent;
6) adding sterile water into the centrifuge tube to wash the target cells twice, centrifuging, and discarding liquid;
7) adding the mixed enzyme treatment agent into the centrifuge tube to treat the target cells at 35-45° C. for 3-12 h;
8) subjecting the centrifuge tube to a centrifugation to collect the target cells to a bottom of the centrifuge tube, then discarding liquid; and
9) adding PBS (phosphate-buffered saline) into the centrifuge tube to wash the target cells once, centrifuging, discarding liquid, and retaining 4-10 µl of cell suspension;
(3) extraction fungal gDNA from the fungal protoplasm and amplification of the fungal gDNA: using a single-cell whole genome amplification kit to perform a nucleic acid extraction and amplification reaction on the 4-10 µl cell suspension obtained in the step 9) to obtain the fungal gDNA;
(4) library construction of trace gDNA: constructing a library of the fungal gDNA using a DNA library construction kit;
(5) genome sequencing: performing whole genome sequencing on the fungal gDNA after constructing the library; and
(6) bioinformatics analysis: assembling data obtained from sequencing by using a relevant software to obtain assembled results, and the assembled results are compared with a relevant public database to determine a species of the trace fungi.

2. The method for detecting the trace fungi using the single-cell sequencing according to claim 1, wherein the trace fungi are selected from the group consisting of *Candida albicans, Candida glabrata, Candida krusei, Candida tropicalis, Candida parapsilosis,* and *Candida dubliniensis*, within the genus *Candida; Aspergillus fumigatus, Aspergillus flavus, Aspergillus terreus, Aspergillus nidulans, Aspergillus niger,* and *Aspergillus ustus*, within the genus *Aspergillus; Cryptococcus neoformans* and *Cryptococcus gattii*, within the genus *Cryptococcus*.

3. The method for detecting the trace fungi using the single-cell sequencing according to claim 1, wherein the trace fungi comprise *Malassezia* sp.

4. The method for detecting the trace fungi using the single-cell sequencing according to claim 1, wherein the trace fungi are selected from the group consisting of *Histoplasma* sp., *Emmonsia* sp., *Sporothrix schenckii, Penicillium marneffei, Paracoccidiodes brasiliensis, Blastomycosis dermatitidis,* and *Coccidioides immitis*.

5. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 6 mg/mL of snail enzyme, and the 4 mg/mL of lywallzyme;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent to treat the target cells at 37° C. for 6 h;
8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 4 µl of the cell suspension.

6. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 6 mg/mL of snail enzyme, and the 4 mg/mL of lywallzyme;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 45° C. for 10 h;

8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 5 μl of the cell suspension.

7. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 4 mg/mL of snail enzyme, the 4 mg/mL of lywallzyme, and the 4 mg/mL of lysozyme;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 35° C. for 8h;
8) subjecting the centrifuge tube to the centrifugation to collect the target cells to the bottom of the centrifuge tube, then discarding the liquid; and
9) adding the PBS into the above-mentioned centrifuge tube to wash the target cells once, centrifuging, discarding the liquid, and retaining 6 μl of the cell suspension.

8. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 4 mg/mL of snail enzyme, the 3 mg/mL of lywallzyme, and the 3 mg/mL of cellulase;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 37° C. for 3 h;
8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 6 μl of the cell suspension.

9. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 4 mg/mL of snail enzyme, the 3 mg/mL of lysozyme, and the 3 mg/mL of cellulase;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 37° C. for 12 h;
8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 8 μl of the cell suspension.

10. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 5 mg/mL lywallzyme, the 4 mg/mL of lysozyme, and the 3 mg/mL of cellulase;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 37° C. for 6 h;
8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 10 μl of the cell suspension.

11. The method for detecting the trace fungi using the single-cell sequencing according to claim 1, wherein the step (2) is as follows:
(2) wall-breaking of the fungi cell walls: extraction of the fungal protoplasm by the chemical method combined with the mixed enzymatic method:
1) adding the 0.8 M D-sorbitol solution into the centrifuge tube containing the target cells to immerse the target cells at 4° C. for 2 h;
2) preparation of the composite pretreatment agent: mixing the 50 mM Tris, the 5 mM EDTA and the 5% (β-mercaptoethanol evenly;
3) preparation of the mixed enzyme treatment agent: mixing the 4 mg/mL of snail enzyme, the 2 mg/mL of lywallzyme, the 3 mg/mL of lysozyme, and the 4 mg/mL of cellulase;
4) adding the composite pretreatment agent into the centrifuge tube to treat the target cells at 35° C. for 1 h;
5) subjecting the centrifuge tube to the centrifugation to collect the target cells to the bottom of the centrifuge tube, then discarding the composite pretreatment agent;
6) adding the sterile water to wash the target cells twice, centrifuging, and discarding the liquid;
7) adding the mixed enzyme treatment agent into the centrifuge tube to treat the target cells at 37° C. for 6 h;
8) subjecting the centrifuge tube to the centrifugation to collect the target cells to the bottom of the centrifuge tube, then discarding the liquid; and
9) adding the PBS into the centrifuge tube to wash the target cells once, centrifuging, discarding the liquid, and retaining 6 μl of the cell suspension.

12. The method for detecting the trace fungi using the single-cell sequencing according to claim 5, wherein the trace fungi are selected from the group consisting of *Candida albicans, Candida glabrata, Candida krusei, Candida tropicalis, Candida parapsilosis*, and *Candida dubliniensis*, within the genus *Candida; Aspergillus fumigatus, Aspergillus flavus, Aspergillus terreus, Aspergillus nidulans, Aspergillus niger*, and *Aspergillus ustus*, within the genus *Aspergillus; Cryptococcus neoformans* and *Cryptococcus gattii*, within the genus *Cryptococcus*.

13. The method for detecting the trace fungi using the single-cell sequencing according to claim 5, wherein the trace fungi comprise *Malassezia* sp.

14. The method for detecting the trace fungi using the single-cell sequencing according to claim 5, wherein the trace fungi are selected from the group consisting of *Histoplasma* sp., *Emmonsia* sp., *Sporothrix schenckii, Penicillium marneffei, Paracoccidiodes brasiliensis, Blastomycosis dermatitidis*, and *Coccidioides immitis*.

15. The method for detecting the trace fungi using the single-cell sequencing according to claim 6, wherein the trace fungi are selected from the group consisting of *Candida albicans, Candida glabrata, Candida krusei, Candida tropicalis, Candida parapsilosis*, and *Candida dubliniensis*, within the genus *Candida; Aspergillus fumigatus, Aspergillus flavus, Aspergillus terreus, Aspergillus nidulans, Aspergillus niger*, and *Aspergillus ustus*, within the genus *Aspergillus; Cryptococcus neoformans* and *Cryptococcus gattii*, within the genus *Cryptococcus*.

16. The method for detecting the trace fungi using the single-cell sequencing according to claim 6, wherein the trace fungi comprise *Malassezia* sp.

17. The method for detecting the trace fungi using the single-cell sequencing according to claim 6, wherein the trace fungi are selected from the group consisting of *Histoplasma* sp., *Emmonsia* sp., *Sporothrix schenckii, Penicillium marneffei, Paracoccidiodes brasiliensis, Blastomycosis dermatitidis*, and *Coccidioides immitis*.

18. The method for detecting the trace fungi using the single-cell sequencing according to claim 7, wherein the trace fungi are selected from the group consisting of *Candida albicans, Candida glabrata, Candida krusei, Candida tropicalis, Candida parapsilosis*, and *Candida dubliniensis*, within the genus *Candida; Aspergillus fumigatus, Aspergillus flavus, Aspergillus terreus, Aspergillus nidulans, Aspergillus niger*, and *Aspergillus ustus*, within the genus *Aspergillus; Cryptococcus neoformans* and *Cryptococcus gattii*, within the genus *Cryptococcus*.

19. The method for detecting the trace fungi using the single-cell sequencing according to claim 7, wherein the trace fungi comprise Malassezia sp.

20. The method for detecting the trace fungi using the single-cell sequencing according to claim 7, wherein the trace fungi are selected from the group consisting of *Histoplasma* sp., *Emmonsia* sp., *Sporothrix schenckii, Penicillium marneffei, Paracoccidiodes brasiliensis, Blastomycosis dermatitidis*, and *Coccidioides immitis*.

\* \* \* \* \*